United States Patent

Werner et al.

[11] 4,137,238
[45] Jan. 30, 1979

[54] PROCESS FOR THE PREPARATION OF 2-HYDROXYCARBAZOLES

[75] Inventors: Friedrich Werner, Cologne; Rolf Pütter, Dusseldorf; Peter Wenzl, Cologne, all of Germany

[73] Assignee: Bayer Aktiengesellschaft, Leverkusen, Germany

[21] Appl. No.: 883,980

[22] Filed: Mar. 6, 1978

[30] Foreign Application Priority Data

Mar. 18, 1977 [DE] Fed. Rep. of Germany ....... 2711943

[51] Int. Cl.² ............................................. C07D 209/88
[52] U.S. Cl. ................................................... 260/315
[58] Field of Search ......................................... 260/315

[56] References Cited
PUBLICATIONS

Sumpter et al., "Heterocyclic Compounds with Indole and Carbazole Systems" (1954), Interscience Publishers Inc., New York, p. 73.

*Primary Examiner*—Henry R. Jiles
*Assistant Examiner*—R. W. Ramsuer
*Attorney, Agent, or Firm*—Sprung, Felfe, Horn, Lynch & Kramer

[57] ABSTRACT

A process for the preparation of a 2-hydroxycarbazole of the formula

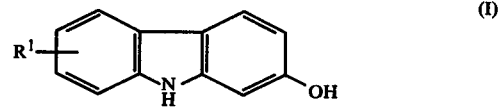

(I)

wherein
  $R^1$ represents hydrogen, halogen or an optionally substituted alkyl, aryl or alkoxy radical which comprises contacting a diphenylamine of the formula

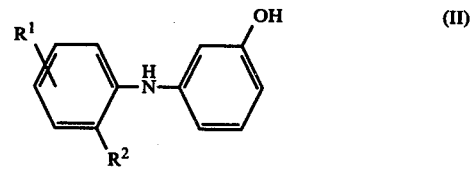

(II)

wherein
  $R^1$ has the above-described meaning and
  $R^2$ represents halogen with a base at an elevated temperature in water and/or an organic solvent or diluent.

7 Claims, No Drawings

PROCESS FOR THE PREPARATION OF 2-HYDROXYCARBAZOLES

BACKGROUND OF THE INVENTION

Field of the Invention

The invention relates to a process for the preparation of 2-hydroxycarbazoles.

SUMMARY OF THE INVENTION

A process has been found for the preparation of a 2-hydroxycarbazole of the formula

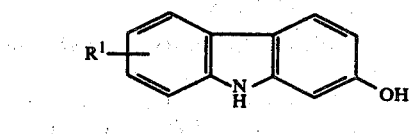  (I)

wherein
$R^1$ represents hydrogen, halogen or an optionally substituted alkyl, aryl or alkoxy radical,
comprising treating a diphenylamine of the formula

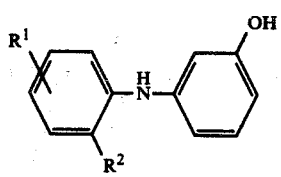  (II)

wherein
$R^1$ has the abovementioned meaning and
$R^2$ represents halogen
with a base at an elevated temperature in the presence of water and/or an organic solvent or diluent.

A possible optionally substituted alkyl radical ($R^1$) is a straight-chain or branched radical with up to 8, preferably with up to 4, carbon atoms. Examples which may be mentioned are the following alkyl radicals: methyl, ethyl, n-propyl, iso-propyl, n-butyl, iso-butyl and tert.-butyl.

A possible optionally substituted aryl radical ($R^1$) is a carbocyclic aromatic ring with 6 to 12 carbon atoms. Examples which may be mentioned are the following aryl radicals: phenyl, 2-methylphenyl, 4-methylphenyl and naphthyl, the phenyl radical being particularly preferred.

A possible optionally substituted alkoxy radical ($R^1$) is an alkoxy radical which has a straight-chain or branched aliphatic hydrocarbon radical with up to 8, preferably 4, carbon atoms. Examples of alkoxy radicals which may be mentioned are: methoxy, ethoxy, propoxy and butoxy.

Examples of halogens ($R^2$) which may be mentioned are fluorine, chlorine and bromine, chlorine and bromine being particularly preferred.

Preferred compounds of the formula (II) are diphenylamines of the formula

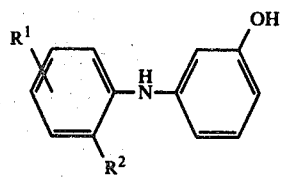  (II)

wherein
$R^1$ represents hydrogen and
$R^2$ represents chlorine or bromine.

The preparation of the diphenylamines according to formula (II) is in itself known, for example from resorcinol and chloroaniline (German Reichspatent No. 515,208 and Frdl. 17, 491).

The following diphenylamines may be mentioned as examples: 2-chloro-3'-hydroxydiphenylamine, 2,4-dichloro-3'-hydroxydiphenylamine, 2-chloro-4-methyl-3'-hydroxydiphenylamine and 2-chloro-4'-methoxy-3-hydroxydiphenylamine.

The process according to the invention can be illustrated using the example of the treatment of 2-chloro-3'-hydroxydiphenylamine with sodium hydroxide:

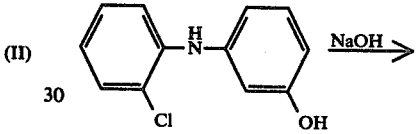

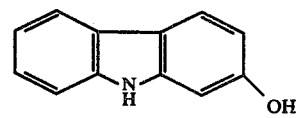

The process according to the invention can be carried out in water and/or a solvent or diluent, the weight ratio of water to solvent or diluent in a water/solvent mixture or water/diluent mixture being about 0.05 to 50, preferably 0.1 to 5.

Solvents or diluents which can be used are high-boiling phenol ethers with up to 20, preferably 12, carbon atoms. Examples which may be mentioned are: diphenyl ether, methyl phenyl ether, ethyl phenyl ether, propyl phenyl ether and butyl phenyl ether.

Cyclic sulphones can be mentioned as further solvents or diluents which can be employed within the scope of the process according to the invention, for example tetramethylene sulphone (sulpholane), pentamethylene sulphone, 2-methyl-tetramethylene sulphone and hexamethylene sulphone.

Furthermore, possible solvents or diluents are tertiary amines with up to 20 carbon atoms, preferably up to 12 carbon atoms, such as N,N-dimethylaniline, N,N-diethylaniline and N,N-dipropylaniline.

Possible bases which can be employed within the scope of the process according to the invention are the hydroxides, carbonates, alcoholates, phenolates and/or bicarbonates of the elements of the first and/or second main group of the periodic system and/or the salts of amines and/or of amides of aliphatic and/or aromatic carboxylic acids with up to 12 carbon atoms, which are derived from the elements of the first and/or second main group of the periodic system.

Examples which may be mentioned of elements of the first and/or second main group of the periodic system are: lithium, sodium, potassium, magnesium and calcium.

Possible alcoholates are those with up to 12 carbon atoms, preferably up to 5 carbon atoms, such as methylate, ethylate, propylate, butylate and amylate.

Suitable amines which may be mentioned are aliphatic or aromatic amines with up to 12 carbon atoms, preferably up to 8 carbon atoms, such as dimethylamine, ethylamine, aniline and N-methylaniline.

Suitable amides which may be mentioned are amides of aromatic or aliphatic carboxylic acids with up to 12 carbon atoms, preferably with up to 6 carbon atoms, such as acetic acid amide, propionic acid amide and benzoic acid amide.

Particularly suitable bases for the process according to the invention are the hydroxides and/or alcoholates of the elements of the first and/or second main group of the periodic system, the sodium compounds being particularly advantageous.

The bases can be employed either individually or in mixtures with one another. The mixing ratio of the bases with one another is not critical here.

In general, the bases are employed in 0.1 to 10 times the molar amount, preferably in 1 to 5 times the molar amount, relative to the molar amount of the diphenylamine compounds.

In general, the process according to the invention can be carried out at a reaction temperature of about 150° to 400° C., preferably of about 210° to 350° C.

The process according to the invention can be carried out discontinuously and continuously.

Advantages of the process according to the invention which may be mentioned are its simple procedure in a single process step and its ecological acceptability.

The 2-hydroxycarbazoles prepared by the process according to the invention are valuable intermediate products for dyestuffs (German Reichspatent No. 551,880).

The process is illustrated with the aid of the following examples.

EXAMPLE 1

219.5 g (1 mol) of 2-chloro-3'-hydroxydiphenylamine are stirred with 120 g (3 mols) of NaOH and 12,800 g of $H_2O$ for 7 hours at 270° C. After cooling, the reaction mixture is rendered acid (pH 1) with concentrated hydrochloric acid and the product which has precipitated is filtered off, washed and dried. This gives 180 g of product which consists of 2-hydroxycarbazole to the extent of 70% = 68.9% of theory.

EXAMPLE 2

254 g (1 mol) of 2,4-dichloro-3'-hydroxydiphenylamine are stirred with 120 g (3 mols) of NaOH and 12,800 g of $H_2O$ for 7 hours at 250° C. The mixture is acidified to pH 1 with hydrochloric acid and the precipitate is filtered off. After drying, 200 g of product are obtained which has a content of 2-hydroxy-7-chlorocarbazole of 60%. Sublimation and subsequent recrystallisation from acetic acid gives 98 g = 45.7% of theory; melting point 177° C.

EXAMPLE 3

233.5 g (1 mol) of 2-chloro-5-methyl-3'-hydroxydiphenylamine are stirred with 160 g (4 mols) of NaOH and 12,800 g of $H_2O$ for 10 hours at 290° C. The mixture is adjusted to pH 1 with hydrochloric acid and the precipitate which has separated out is filtered off and dried. Sublimation and subsequent crystallisation from acetic acid gives 111 g = 56.4% of theory of 2-hydroxy-5-methylcarbazole; melting point 191° C.

EXAMPLE 4

219.5 g (1 mol) of 2-chloro-3'-hydroxydiphenylamine are slowly heated to 250° C. with 108 g (2 mols) of sodium methylate in 6 liters of diphenyl ether. The mixture is kept at this temperature for 7 hours and the diphenyl ether is then distilled off.

The residue is suspended in $H_2O$ and the suspension is rendered acid (pH 1) with concentrated hydrochloric acid and filtered. This gives 185 g of product which consists of 2-hydroxycarbazole to the extent of 48%.

EXAMPLE 5

219.5 g (1 mol) of 2-chloro-3'-hydroxydiphenylamine are dissolved in 6,000 g of sulpholane at 80° C. 30 g of $H_2O$ and 80 g (2 mols) of NaOH are added to the solution. The mixture is heated to 230° C. for five hours. Thereafter, the water and then the sulpholane are distilled off in vacuo. The residue is suspended in 1 liter of $H_2O$. The suspension is acidified with HCl and filtered and the residue is dried. This gives 185 g of product which consists of 2-hydroxycarbazole to the extent of 37% = 37.8% of theory.

EXAMPLE 6

219.5 g (1 mol) of 2-chloro-3'-hydroxydiphenylamine are added to 10,000 g of $H_2O$. 2,000 g of sulpholane and 120 g of NaOH are added to the suspension. The mixture is heated to 270° C. for five hours. Thereafter, the solution is rendered acid (pH 1) with HCl and the precipitate which has separated out is filtered off and dried. 190 g of product are isolated with a content of 2-hydroxycarbazole of 64% = 66.4% of theory.

EXAMPLE 7

219.5 g (1 mol) of 2-chloro-3'-hydroxydiphenylamine are dissolved in 12,800 g of $H_2O$ with 168 g (3 mols) of KOH. The solution is heated to 250° C. for five hours. After cooling, it is rendered acid (pH 1) with HCl and the precipitate is filtered off and dried. This gives 172 g of product which consists of 2-hydroxycarbazole to the extent of 62% = 58.2% of theory.

EXAMPLE 8

219.5 g (1 mol) of 2-chloro-3'-hydroxydiphenylamine are dissolved in 12,800 g of $H_2O$ with 40 g of NaOH and 424 g (4 mols) of $Na_2CO_3$. The solution is heated to 280° C. for 7 hours. After cooling, it is acidified (pH 1) with HCl and the precipitate is filtered off. 178 g of product are obtained which has a content of 2-hydroxycarbazole of 68% = 66.1% of theory.

EXAMPLE 9

219.5 g (1 mol) of 2-chloro-3'-hydroxydiphenylamine are dissolved in 12,800 g of $H_2O$ with 120 g (3 mols) of NaOH. The solution is heated to 350° C. for 5 minutes. It is cooled and rendered acid (pH 1) with HCl. The residue is filtered off and dried. This gives 170 g of product which consists of 2-hydroxycarbazole to the extent of 70% = 65.1% of theory.

What is claimed is:

1. A process for the preparation of a 2-hydroxycarbazole of the formula

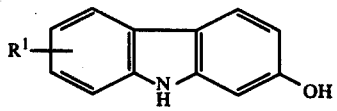

(I)

wherein
 $R^1$ represents hydrogen, halogen or an optionally substituted alkyl, aryl or alkoxy radical
which comprises contacting a diphenylamine of the formula

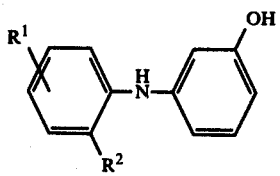

(II)

wherein
 $R^1$ has the above-described meaning and
 $R^2$ represents halogen
with a base at an elevated temperature of from 150° to 400° C. in water and/or an organic solvent or diluent the ratio of base to diphenylamine being 0.1 to 10 the molar amount relative to diphenylamine.

2. A process according to claim 1 wherein $R^1$ represents hydrogen and $R^2$ represents chlorine or bromine.

3. A process according to claim 1 carried out in the presence of a solvent or diluent which is a phenol ether, a cyclic sulfone or a tertiary amine.

4. A process according to claim 1 wherein the process is carried out in the presence of diphenyl ether and/or sulfolane.

5. A process according to claim 1 wherein the base is a hydroxide, carbonate, alcoholate, phenolate or bicarbonate of an element of the first and/or second main group of the Periodic System.

6. A process according to claim 1 wherein the base is sodium methylate, sodium hydroxide, potassium hydroxide and/or sodium carbonate.

7. A process according to claim 1 wherein the reaction is carried out at a temperature of 210° to 350° C.

* * * * *